United States Patent
Yuen et al.

(12) 
(10) Patent No.: US 6,180,781 B1
(45) Date of Patent: *Jan. 30, 2001

(54) PROCESS FOR MAKING MOMETASONE FUROATE MONOHYDRATE

(75) Inventors: Pui-Ho Yuen, Princeton Junction; Charles Eckhart, Kenilworth; Teresa Etlinger, Bloomfield; Nancy Levine, Flemington, all of NJ (US)

(73) Assignee: Schering Corporation, Kenilworth, NJ (US)

( * ) Notice: Under 35 U.S.C. 154(b), the term of this patent shall be extended for 0 days.

This patent is subject to a terminal disclaimer.

(21) Appl. No.: 08/422,479

(22) Filed: Apr. 17, 1995

Related U.S. Application Data

(63) Continuation of application No. 07/984,573, filed as application No. PCT/US91/06249 on Sep. 6, 1991, which is a continuation of application No. 07/580,239, filed on Sep. 10, 1990, now abandoned.

(51) Int. Cl.[7] .................................................. C07J 17/00
(52) U.S. Cl. ............................................................ 540/114
(58) Field of Search .............................. 540/114; 514/172

(56) References Cited

U.S. PATENT DOCUMENTS

| 4,472,393 | 9/1984 | Shapiro .................................. 540/115 |
| 4,775,529 | 10/1988 | Sequeira et al. ...................... 514/171 |
| 4,783,444 | 11/1988 | Watkins et al. ......................... 514/19 |

FOREIGN PATENT DOCUMENTS

| 0262681 | 4/1988 | (EP) . |
| 9204365 * | 3/1992 | (WO) .............................. C07J/17/00 |

OTHER PUBLICATIONS

Bristol–Myers Co. v. US Int'l Trade Commission, 15USPQ2d 1258 (1989).*
In re Certain Crystalline Cefadioxil Monohydrate, 15USPQ2d 1263 (1990).*

* cited by examiner

*Primary Examiner*—Barbara Badio
(74) *Attorney, Agent, or Firm*—John J. Maitner; Carl W. Battle; Robert A. Franks

(57) ABSTRACT

The invention relates to the novel compound mometasone furoate monohydrate, process for its preparation and pharmaceutical compositions containing said compound.

7 Claims, 2 Drawing Sheets

PROCESS FOR MAKING MOMETASONE FUROATE MONOHYDRATE

This is a continuation of application Ser. No. 07/984,573, filed Mar. 5, 1993, which is a 371 of PCT/US91/06249, filed Sep. 6, 1991, which is a continuation of application Ser. No. 07/580,239, filed Sep. 10, 1990, now abandoned.

BACKGROUND OF THE INVENTION

The present invention relates to a novel composition of matter, 9α, 21-dichloro-16α-methyl-1,4-pregnadiens-11β, 17α-diol-3,20-dione-17-(2'-furoate) monohydrate, also designated mometasone furoate monohydrate, process for its preparation, and pharmaceutical preparation thereof.

Mometasone furoate is known to be useful in the treatment of inflammatory conditions. The compound is prepared by procedures disclosed in U.S. Pat. No. 4,472,393, which patent is hereby incorporated by reference.

When aqueous pharmaceutical compositions, e.g. suspensions, containing anhydrous mometasone furoate were subjected to stability testing by rotating for four weeks at room temperature and 35° C., formation of a crystalline material which is different from the anhydrous mometasone furoate crystal was observed in suspension. Experiments were designed to determine the nature of the crystalline material. It was postulated that formulation of mometasone furoate compositions with the stable crystalline form would reduce the probability of crystal growth during long term storage of the suspension leading to a more stable product.

SUMMARY OF THE INVENTION

The present invention provides mometasone furoate monohydrate of formula I

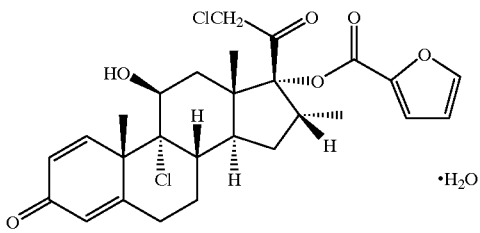

a process for preparing said compound by crystallization from a saturated aqueous water miscible organic solution. The present invention also provides aqueous stable pharmaceutical compositions of mometasone furoate monohydrate.

DETAILED DESCRIPTION OF THE INVENTION

Figure 1:
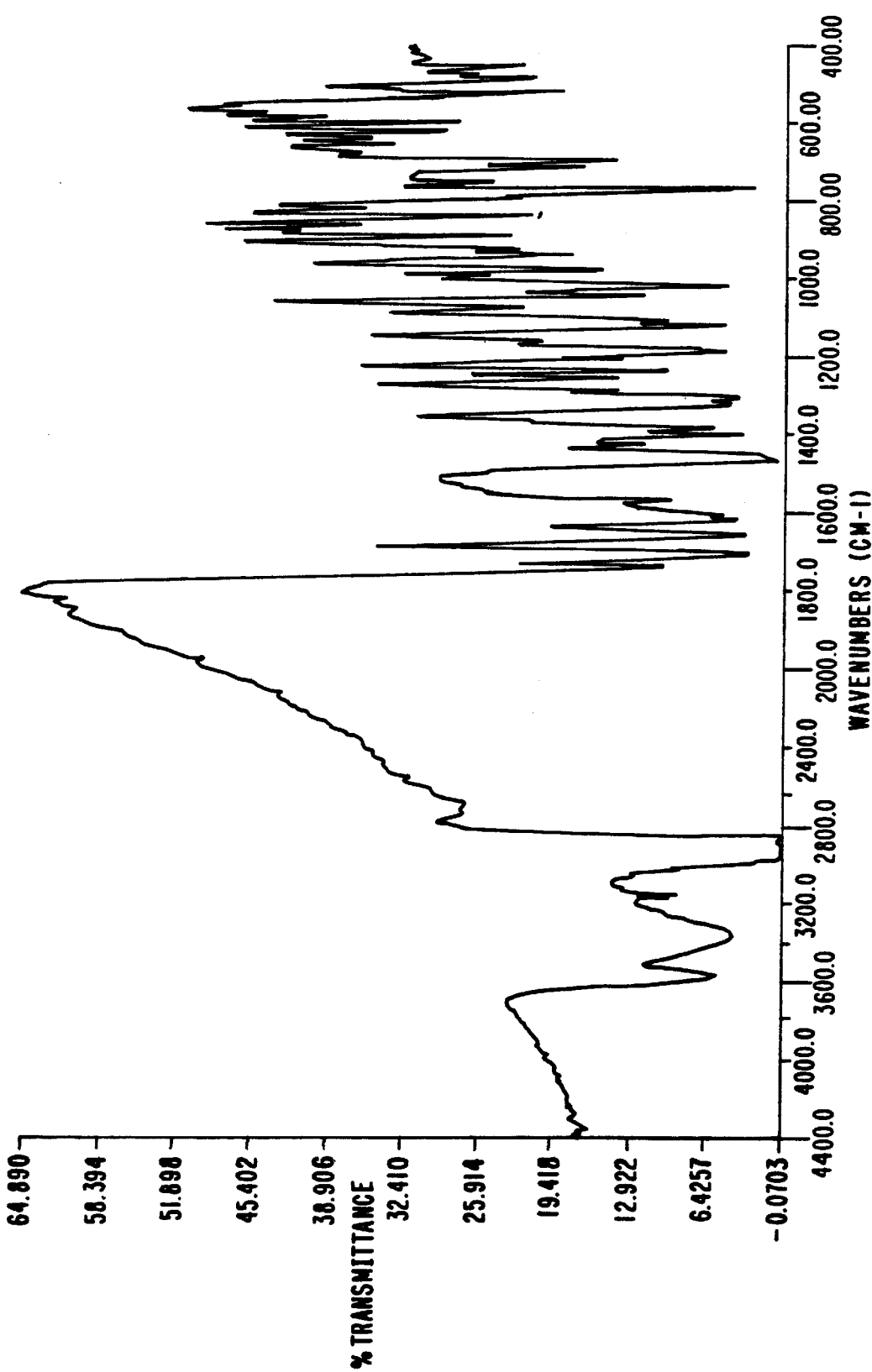
FIG. 1: Infrared spectrum of crystalline mometasone furoate monohydrate

The composition of matter of the present invention, mometasone furoate monohydrate has the following characteristics.

| Molecular formula | $C_{27}H_{30}Cl_2O_6 \cdot H_2O$ |
| --- | --- |
| Formula weight | 539.46 |
| Elemental Analysis (theory) | C = 60.11%, H = 5.98%; Cl = 13.16% |
| (found) | C = 59.99%; H = 5.56%; Cl = 13.17% |
| Water Analysis (% $H_2O$) (theory) | 3.34% |
| (found) | 3.31, 3.47 |

The crystalline mometasone furoate monohydrate exhibits an x-ray crystallographic powder diffraction pattern having essentially the values as shown in Table I.

TABLE I

| Angle of 2θ (degrees) | Spacing d (Å) | Relative Intensity I/I |
| --- | --- | --- |
| 7.795 | 11.3324 | 100 |
| 11.595 | 7.6256 | 6 |
| 12.035 | 7.3478 | 3 |
| 12.925 | 6.8437 | 11 |
| 14.070 | 6.2893 | 22 |
| 14.580 | 6.0704 | 5 |
| 14.985 | 5.9072 | 12 |
| 15.225 | 5.8146 | 33 |
| 15.635 | 5.6631 | 96 |
| 16.710 | 5.3011 | 15 |
| 17.515 | 5.0592 | 14 |
| 18.735 | 4.7324 | 12 |
| 20.175 | 4.3978 | 13 |
| 20.355 | 4.3593 | 6 |
| 20.520 | 4.3246 | 4 |
| 21.600 | 4.1108 | 5 |
| 21.985 | 4.0396 | 22 |
| 22.420 | 3.9622 | 8 |
| 22.895 | 3.8811 | 7 |
| 23.245 | 3.8234 | 14 |
| 23.550 | 3.7746 | 13 |
| 24.245 | 3.6680 | 4 |
| 24.795 | 3.5878 | 11 |
| 24.900 | 3.5729 | 5 |
| 25.800 | 3.4503 | 5 |
| 25.985 | 3.4262 | 3 |
| 26.775 | 3.3268 | 84 |
| 27.170 | 3.2794 | 10 |
| 27.305 | 3.2635 | 9 |
| 27.710 | 3.2167 | 5 |
| 28.385 | 3.1417 | 7 |
| 29.165 | 3.0594 | 1 |
| 29.425 | 3.0330 | 2 |
| 29.725 | 3.0030 | 2 |
| 30.095 | 2.9670 | 7 |
| 30.255 | 2.9516 | 3 |
| 30.490 | 2.9294 | 10 |
| 30.725 | 2.9075 | 6 |
| 31.115 | 2.8720 | 3 |
| 31.595 | 2.8294 | 47 |
| 32.135 | 2.7831 | 6 |
| 32.985 | 2.7133 | 7 |
| 33.400 | 2.6805 | 2 |
| 33.820 | 2.6482 | 2 |
| 34.060 | 2.6301 | 8 |
| 34.625 | 2.5885 | 4 |
| 34.795 | 2.5762 | 2 |
| 35.315 | 2.5394 | 1 |
| 36.780 | 2.4416 | 21 |
| 37.295 | 2.4090 | 2 |

Single crystal data of mometasone furoate monohydrate exhibits the following values as shown in Table II.

TABLE II

Crystallographic Data[a]

| Crystal system | triclinic |
|---|---|
| Space group | $\underline{P}1(C_1^1)$-No.1 |
| $\underline{a}$(Å) | 8.481(1) |
| $\underline{b}$(Å) | 11.816(2) |
| $\underline{c}$(Å) | 7.323(1) |
| α(°) | 95.00(1) |
| β(°) | 110.66(1) |
| γ(°) | 73.27(1) |
| $\underline{V}$(Å³) | 657.5(3) |
| $\underline{D}$calcd.(g cm⁻³) | 1.362 |

[a]An Enraf-Nonius CAD-4 diffractometer (Cu-$\underline{K}$α radiation, incident-beam graphite monochromator) was used for all measurements, Intensity data were corrected for the usual Lorentz and polarization effects; an empirical absorption correction was also applied.

The crystal structure was solved by direct methods (RANTAN). Approximate non-hydrogen atom positions were derived from an E-map. Hydrogen atoms were located in a series of difference Fourier syntheses evaluated following several rounds of full-matrix least-squares adjustment of non-hydrogen atom positional and anisotropic temperature factor parameters. Hydrogen atom positional and isotropic thermal parameters were included as variables in the later least-squares iterations which also involved refinement of an extinction correction. Crystallographic calculations were performed on PDP11/44 and MicroVAX computers by use of the Enfra-Nonius Structure Determination Package (SDP). For all structure-factor calculations, neutral atom scattering factors and their anomalous dispersion corrections were taken from *International Tables for X-Ray Crystallography*, vol. IV, The Knynock Press, Birmingham, England, 1974.

Mometasone furoate monohydrate can be prepared by forming a saturated homogeneous solution of anhydrous mometasone furoate in a mixture of water and a water miscible organic solvent. The saturated solution is prepared by dissolving the mometasone furoate in a water miscible organic solvent at the temperature of about 85° C. Hot water, about 85° C., is added dropwise with agitation. After removing the solution from the steam bath, the reaction is stirred for about one hour and then allowed to stand undisturbed overnight while cooling to room temperature. The solution is stirred while adding additional water at room temperature and the solution becomes cloudy and a white precipitate forms. The reaction is allowed to stir for a time, the preciptitate collected by filtration and the product dried to constant weight.

Organic solvents that can be employed in the process of this invention must be miscible with water and one in which mometasone furoate is soluble. Examples of water miscible organic solvents include alcohols, such as, ethanol, isopropanol, and the like; ketones, such as acetone, and the like; ethers, such as dioxane, and the like; esters such as ethyl acetate, and the like. The preferred solvents are acetone and isopropanol.

In another aspect, the present invention provides pharmaceutical compositions comprising mometasone furoate monohydrate of formula I in an inert pharmaceutically acceptable carrier or diluent.

The pharmaceutical compositions according to the invention can be prepared by combining mometasone furoate. monohydrate with any suitable inert pharmaceutical carrier or diluent and administered orally, parentally or topically in a variety of formulations.

Of particular interest are aqueous suspension compositions of mometasone furoate monohydrate, e.g. for nasal administration. The aqueous suspensions of the invention may contain from 0.1 to 10.0 mg of mometasone furoate monohydrate per gram of suspension.

The aqueous suspension compositions according to the present invention may contain, inter alia, auxiliaries and/or more of the excipients, such as: suspending agents, e.g. microcrystalline cellulose, sodium carboxymethylcellulose, hydroxypropyl-methyl cellulose; humectants, e.g. glycerin and propylene glycol; acids, bases or buffer substances for adjusting the pH, e.g. citric acid, sodium citrate, phosphoric acid, sodium phosphate e.g. citrate and phosphate buffers; surfactants, e.g. Polysorbate 80; and antimicrobial preservatives, e.g. benzalkonium chloride, phenylethyl alcohol and potassium sorbate.

The following examples illustrate the present invention and the best made of practicing the process of the invention. It will be apparent to those skilled in the art that modifications thereof may be practical without departing from the purpose and intent of this disclosure.

GENERAL EXPERIMENTAL

Infrared absorption spectra were taken as Nujol Mull on a Nicolet FT-Infrared spectrometer Model No. 5DXB. X-ray crystallograph powder diffraction patterns were taken on a Philips X-ray diffractometer Model APD-3720 equipped with a radiation source: copper Kα. Decomposition temperatures were measured on a Dupont differential scanning calorimeter, Model No. 990.

Moisture content of the crystalline mometasone furoate monohydrate was determined by titration with Karl Fisher reagent.

EXAMPLE 1

Figure 2:
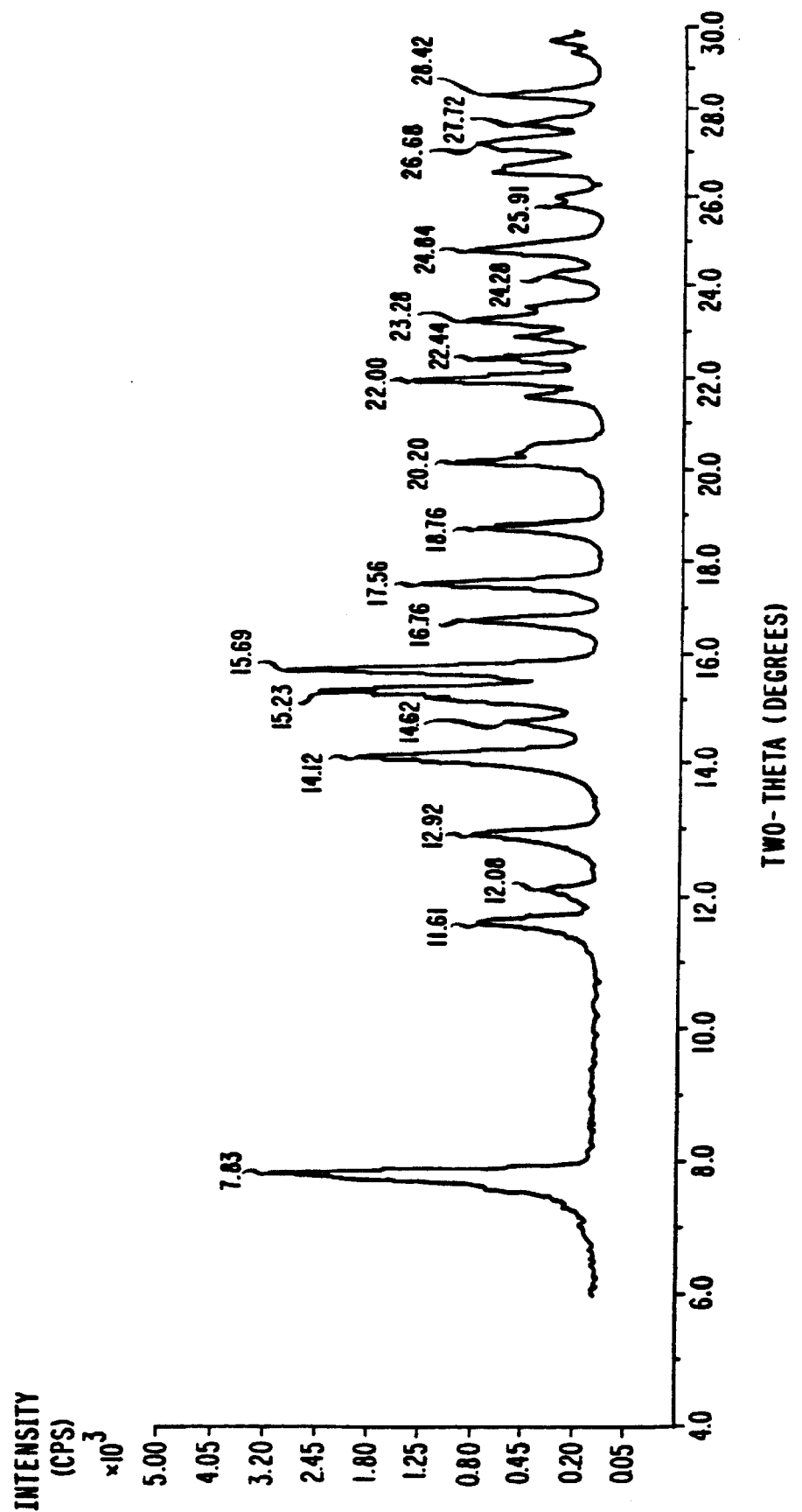
FIG. 2: X-ray diffraction pattern of crystalline mometasone furoate monohydrate

Place 4.5 liters of ethyl alcohol into a suitable vessel equipped with an appropriate agitator and closure. Dissolve 27 g of mometasone furoate anhydrous powder into the ethanol with stirring. Filter the saturated solution and slowly add purified water about 1.5 liters, at a flow rate of approximately 50 ml/minute while stirring at moderate speed. When the solvent mixture reaches a ratio of 1:3 (water:ethanol), the addition of water is stopped and stirring of the reaction mixture is continued for approximately 2 hours to facilitate seeding. Resume addition of water, about 7.5 liters at a rate of approximately 50 ml/minute, until a ratio of 2:1 (water:ethanol) is achieved. Continue stirring to complete crystallization. The crystals are collected by filtration and dried in a vacuum desiccator at room temperature to afford 24.83 g of mometasone furoate monohydrate having an infrared spectrum and X-ray diffraction graph substantially the same as that in FIGS. 1 and 2.

EXAMPLE 2

Place 24.3 liters of 2-propanol into a suitable container. Dissolve 340 grams of anhydrous mometasone furoate in the 2-propanol by heating the mixture (steam bath) to 85° C. with stirring. After the furoate has dissolved, add dropwise with stirring over 15 minutes 1950 ml of hot (85° C.) water. The hot solution is removed from the steam bath and the solution is stirred for 1 hour. The solution is allowed to cool to room temperature overnight without stirring. The remainder of water, about 24 liters is added with stirring; the solution becomes cloudy and a white precipitate begins to form. The reaction is stirred for one hour, following addition of the water. The white precipitate is collected by filtration, washed with 2 liters of water and air dried overnight. The solid is dried in a draft oven at 50° C. to constant weight. Mometasone furoate monohydrate, 316.5 g, weight yield 90%, is obtained having an infrared spectrum and X-ray diffraction graph substantially the same as that in FIGS. 1 and 2.

EXAMPLE 3

An aqueous nasal suspension of mometasone furoate monohydrate is prepared from the following:

| Ingredients | Concentration mg/g | Representative Batch g/12 kg |
|---|---|---|
| Mometasone furoate monohydrate | 0.5 | 6.0 |
| Avicel RC 591* | 20.0 | 240.0 |
| Glycerin | 21.0 | 252.0 |
| Citric Acid | 2.0 | 24.0 |
| Sodium citrate | 2.8 | 33.6 |
| Polysorbate 80** | 0.1 | 1.2 |
| Benzalkonium chloride | 0.2 | 2.4 |
| Phenylethyl alcohol | 2.5 | 30.0 |
| Purified water q.s. ad | 1.0g | 12.0kg |

*Avicel RC-591-is a trademark of FMC for a mixture of microcrystalline cellulose and sodium carboxymethyl cellulose.
**Polysorbate 80 is a tradename for a mixture of an oleate ester of sorbitol and its anhydride copolymerized with approximately 20 moles of ethylene oxide for each mole of sorbitol and sorbitol anhydride.

After dispersing the Avicel RC 591 in 6 kg of purified water, the glycerin is added thereto. The citric acid and sodium citrate is dissolved in 240 ml of water, said solution is added to the Avicel-glycerin dispersion with mixing. In a separate vessel, Polysorbate 80 is dissolved in approximately 400 ml of purified water with stirring. The mometasone furoate monohydrate is dispersed in the aqueous Polysorbate 80 solution and; said slurry is then added with stirring to the Avicel-glycerin citric acid mixture. After dissolving benzalkonuim chloride and phenylethyl alcohol in purified water, said solution is added to the suspension mixture with stirring. The suspension is brought to 12 kg with purified water with mixing. The final pH of the suspension is 4.5±0.5.

EXAMPLE 4

The following compositions were prepared without the suspending agent, Avicel RC-591 to prevent interference in X-ray diffraction studies:

| Ingredients | Concentration mg/g | | |
|---|---|---|---|
| | 4A | 4B | 4C |
| Mometasone Furoate Monohydrate Micronized | 0.5 | 0.5 | 0.5 |
| Citric Acid Monohydrate | 2.0 | 2.0 | 2.0 |
| Sodium Citrate Dihydrate | 2.8 | — | 2.8 |
| Sodium Phosphate Dibasic | — | 4.0 | — |
| Polysorbate 80 | 0.1 | 0.1 | 0.1 |
| Benzalkonium Chloride | 0.2 | 0.2 | 0.2 |
| Phenylethyl Alcohol | 2.5 | — | — |
| Potassium Sorbate | — | 3.4 | — |
| Propylene Glycol | — | — | 100.0 |
| Glycerin | 21.0 | 21.0 | 21.0 |
| Water Purified USP q.s. ad | 1.0g | 1.0g | 1.0g |

These compositions were prepared according to the procedure described in Example 3.

The three compositions 4A, 4B and 4C were rotated for five (5) days at 35° C. and a additional four (4) weeks at room temperature to assess crystal form stability. The crystals were isolated from the suspension and X-ray diffraction patterns determined. The results indicated that the crystals collected from each of the three compositions are in the form of mometasone furoate monohydrate.

EXAMPLE 5

The following compositions were prepared and tested to determine thermal stability of said compositions.

| Ingredients | Concentration mg/g | | |
|---|---|---|---|
| | 5A | 5B | 5C |
| Mometasone Furoate Monohydrate Micronized | 0.5 | 0.5 | 0.5 |
| Citric Acid Monohydrate | 2.0 | 2.0 | 2.0 |
| Sodium Citrate Dihydrate | 2.8 | — | 2.8 |
| Sodium Phosphate Dibasic | — | 4.0 | — |
| Polysorbate 80 | 0.1 | 0.1 | 0.1 |
| Benzalkonium Chloride | 0.2 | 0.2 | 0.2 |
| Phenylethyl Alcohol | — | 2.5 | — |
| Potassium Sorbate | — | — | 3.4 |
| Propylene Glycol | 100.0 | — | — |
| Glycerin | 21.0 | 21.0 | 21.0 |
| Avicel RC-591 | 20.0 | 20.0 | 20.0 |
| Water Purified USP q.s. ad | 1.0g | 1.0g | 1.0g |

The compositions were prepared according to the procedure described in Example 3.

The compositions were thermally cycled between 4° C. (24 hours), and 30° C. (24 hours) for a period of one month. Microscopic analyses revealed no detectable mometasone furoate monohydrate crystal growth under these conditions.

We claim:

1. A process for preparing mometasone furoate monohydrate which comprises:
   (a) forming a saturated water-miscible organic solvent solution of mometasone furoate;
   (b) adding sufficient water to form a solvent mixture ratio of at least 1:1 (water:organic solvent); and
   (c) recovering a monohydrate product.

2. The process of claim 1 wherein the organic solvent is selected from the group consisting of ethanol, isopropanol, acetone, dioxane and ethyl acetate.

3. A process for preparing mometasone furoate monohydrate, comprising:
   (a) forming a saturated solution of mometasone furoate in a water-miscible organic solvent;
   (b) adding to the solution an equal or greater volume of water; and
   (c) recovering a monohydrate product.

4. The process of claim 3, wherein the organic solvent is selected from the group consisting of alcohols, ketones. ethers, esters and mixtures of any two or more thereof.

5. The process of claim 3, wherein the organic solvent is selected from the group consisting of ethanol, isopropanol, acetone, dioxane, ethyl acetate and mixtures of any two or more thereof.

6. The process of claim 3, wherein the organic solvent comprises acetone or isopropanol.

7. The process of claim 3, wherein the mometasone furoate monohydrate product is recovered in a yield at least about 90 percent by weight.

* * * * *